United States Patent
Feinberg (10) Patent No.: US 9,474,454 B2
(45) Date of Patent: Oct. 25, 2016

(54) MRI USING FASTER MULTIPLEXED ECHO PLANAR IMAGING (EPI) PULSE SEQUENCES

(71) Applicant: David Feinberg, Sebastapol, CA (US)

(72) Inventor: David Feinberg, Sebastapol, CA (US)

(73) Assignee: ADVANCED MRI TECHNOLOGIES LLC, Sebastopol, CA (US)

( * ) Notice: Subject to any disclaimer, the term of this patent is extended or adjusted under 35 U.S.C. 154(b) by 823 days.

(21) Appl. No.: 13/632,941

(22) Filed: Oct. 1, 2012

(65) Prior Publication Data

US 2013/0181709 A1 Jul. 18, 2013

Related U.S. Application Data (63) Continuation of application No. 13/397,634, filed on Feb. 15, 2012, now abandoned.

(60) Provisional application No. 61/443,215, filed on Feb. 15, 2011, provisional application No. 61/444,031, filed on Feb. 17, 2011, provisional application No. 61/444,039, filed on Feb. 17, 2011.

(51) Int. Cl.
*G01R 33/54* (2006.01)
*A61B 5/026* (2006.01)
(Continued)

(52) U.S. Cl.
CPC ......... *A61B 5/0263* (2013.01); *G01R 33/4835* (2013.01); *G01R 33/543* (2013.01); *G01R 33/56366* (2013.01); *A61B 5/0042* (2013.01); *G01R 33/5616* (2013.01)

(58) Field of Classification Search
CPC ............ G01R 33/4835; G01R 33/543; G01R 33/5616; G01R 33/56366; A61B 5/0042; A61B 5/0263
USPC .......................... 324/300–322; 600/407–422
See application file for complete search history.

(56) References Cited

U.S. PATENT DOCUMENTS 5,578,924 A * 11/1996 Dumoulin .......... G01R 33/4835
  324/309
6,614,225 B1 * 9/2003 Feinberg ...................... 324/307
(Continued)

FOREIGN PATENT DOCUMENTS

WO    WO 2012/054768 A1    4/2012

OTHER PUBLICATIONS

Feinberg DA, et al., Multiplexed Echo Planar Imaging for Sub-Second Whole Brain FMRI and Fast Diffusion Imaging, PLoS One www.plosone.org, Dec. 2010, vol. 5, Issue 12, e15710.

(Continued)

*Primary Examiner* — Melissa Koval
*Assistant Examiner* — Rishi Patel
(74) *Attorney, Agent, or Firm* — Cooper & Dunham, LLP (57) ABSTRACT

An MRI scanner and an MRI method that effectively reduce the inherent difference in timing of TE in the SIR images by using alternating polarity of the slice selective gradient pulse Gs and corresponding alternate polarity in RF phase offset in the excitation pulse. By using alternating polarity selective gradients, the refocusing gradient pulse on the Gs axis can be eliminated between the excitation pulses so that the time spacing between the multiple SIR excitation pulses is reduced, and therefore the time delay between onset of slice signal decay is reduced. This results in an earlier possible TE of the first excited slice, hence less signal decay and higher SNR, and overall the TE of different slices can be more nearly the same.

12 Claims, 10 Drawing Sheets

(51) Int. Cl.
*G01R 33/483* (2006.01)
*G01R 33/563* (2006.01)
*A61B 5/00* (2006.01)
*G01R 33/561* (2006.01)

(56) References Cited

U.S. PATENT DOCUMENTS

2011/0254548 A1* 10/2011 Setsompop et al. .......... 324/309
2012/0056620 A1* 3/2012 Feinberg et al. ............. 324/309

OTHER PUBLICATIONS

Setsompop K, et al., Improving SNR per unit time in Diffusion Imaging using a blipped-CAIPARHINA simultaneous multi-slice EPI acquisition, Proc. Intl. Soc. Mag. Reson, Med. 18 (2010) p. 187.

Souza SP, et al., Simultaneous Multislice Acquisition of MR Images by Hadamard-Encoded Excitation, Journal of Computer Assisted Tomography, 12(6): 1026-1030, Nov./Dec., © 1988 Raven Press, Ltd., New York.

* cited by examiner

MRI USING FASTER MULTIPLEXED ECHO PLANAR IMAGING (EPI) PULSE SEQUENCES

CROSS-REFERENCE TO RELATED APPLICATIONS

This application is a continuation of U.S. patent application Ser. No. 13/397,634 filed Feb. 15, 2012, which claims the benefit of U.S. Provisional Application No. 61/444,031, filed Feb. 17, 2011, U.S. Provisional Application No. 61/444,039, filed Feb. 17, 2011, and U.S. Provisional Application No. 61/443,215, filed Feb. 15, 2011 and the entire contents of each of which are incorporated by reference herein.

FIELD

This patent specification pertains to magnetic resonance imaging (MRI) and, more specifically to providing faster imaging such as by using multiplexed echo planar imaging (EPI) pulse sequences.

BACKGROUND AND SUMMARY OF THE DISCLOSURE

A multiplexed EPI pulse sequence can use a simultaneous image (or echo) refocusing (SIR or SER) technique in which multiple RF excitation pulses excite several slices within the pulse sequence. The MR signals for the several simultaneously excited slices are read out in a single echo train Because the RF pulses in this example are spaced by several milliseconds, e.g., 5 ms, there is a corresponding time difference in their signal decay beginning at their respective excitations. This gives a different TE (echo time, of the time the excitation pulse and the peak of the echo signal in EPI), echo time, and image contrast and SNR (signal to noise ratio) in the MR images. A multiplexed EPI technique is described in Feinberg D A, et al., Multiplexed Echo Planar Imaging for Sub-Second Whole Brain FMRI and Fast Diffusion Imaging, PLoS One www.plosone.org, December 2010, Volume 5, Issue 12, e15710, a paper that is incorporated by reference herein and is attached hereto as Appendix A to become a part of this patent specification.

The inherent difference in timing of TE in the SIR images is effectively reduced according to this patent specification by using alternating polarity of the slice selective gradient pulse Gs and corresponding alternate polarity in RF phase offset in the excitation pulse. By using alternating polarity selective gradients, the refocusing gradient pulse on the Gs axis can be eliminated between the excitation pulses so that the time spacing between the multiple SIR excitation pulses is reduced, and therefore the time delay between onset of slice signal decay is reduced. This results in an earlier possible TE of the first excited slice, hence less signal decay and higher SNR, and overall the TE of different slices can be more nearly the same.

BRIEF DESCRIPTION OF THE DRAWINGS

FIG. 1a illustrates a prior method of using sequential excitation followed by refocusing gradients while

DETAILED DESCRIPTION OF PREFERRED EMBODIMENTS

In describing examples and preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner and features of one embodiment can be used in another.

Figure 1A:
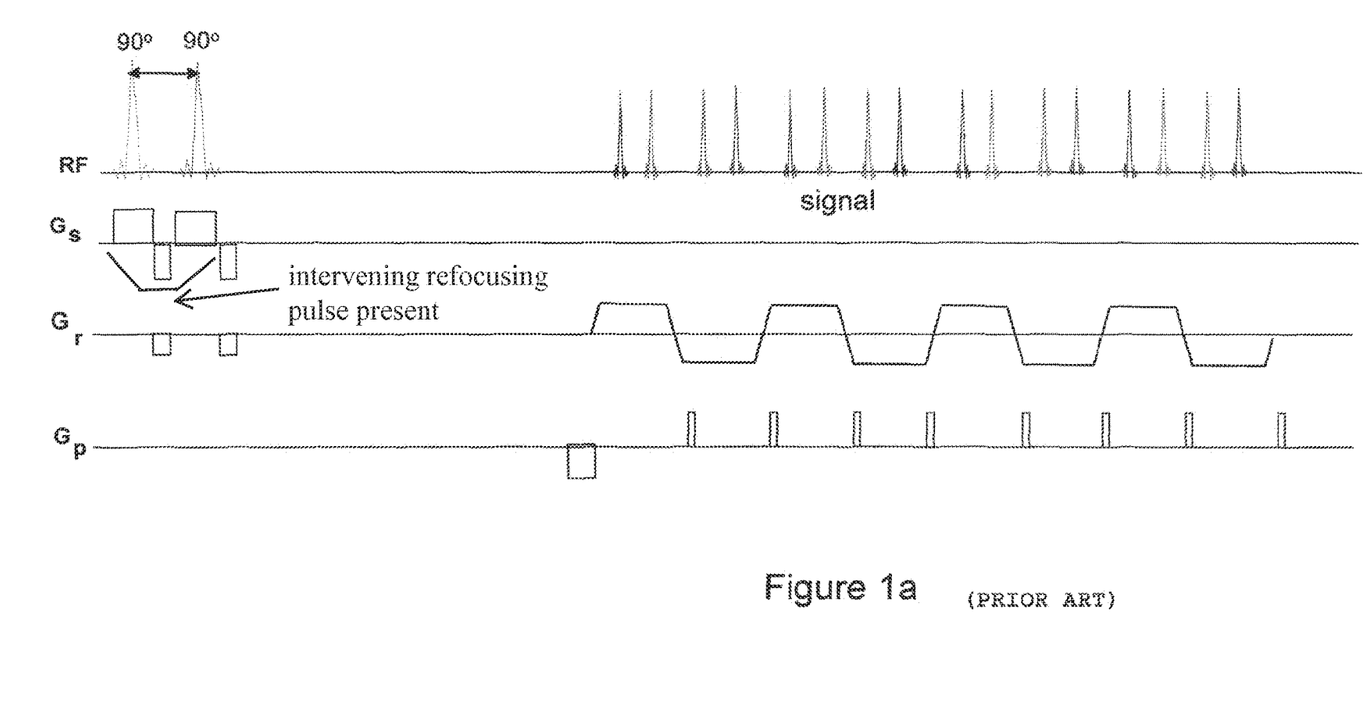
Figure 1B:
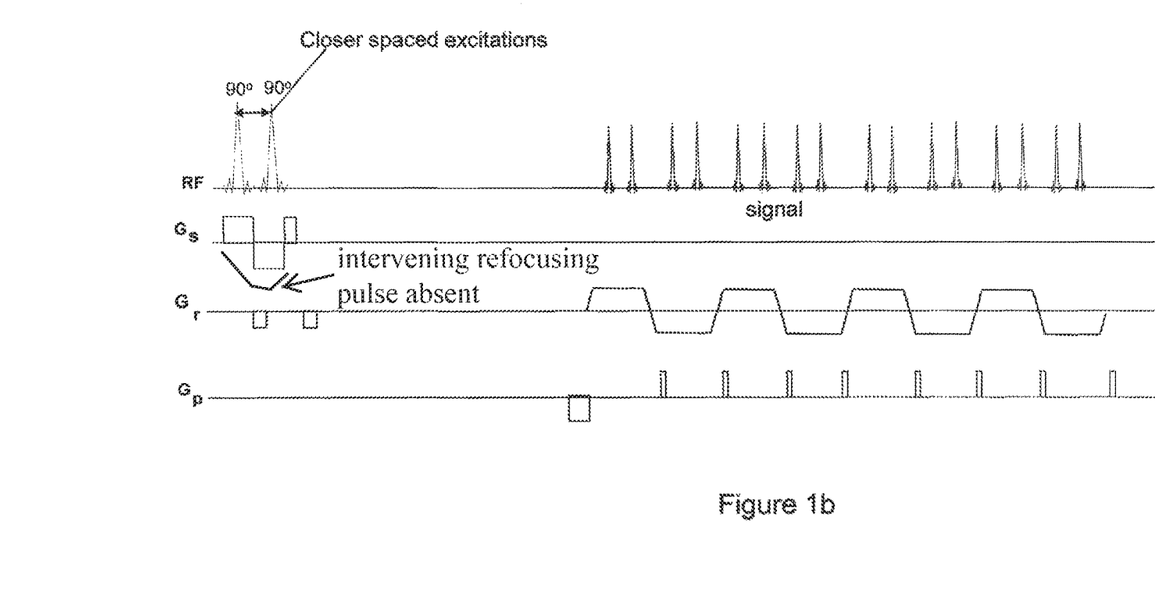
FIG. 1b illustrates a new excitation using alternating polarity Gs gradient pulses without intervening refocusing pulses, thereby shortening the time delays between different slice TEs.

FIG. 1a illustrates a prior method of using sequential excitation followed by refocusing gradients while FIG. 1b illustrates the new excitation using alternating polarity Gs gradient pulses without intervening refocusing pulses, to thereby shorten the time delays between different slice TEs. Whereas in FIG. 1a each of the positive Gs pulse is followed by a negative Gs pulse, in FIG. 1b the Gs pulses are arranged differently. As a non-limiting example, the 90° excitation pulses in FIG. 1a can be spaced by about 5 ms but those in FIG. 1b can be spaced by about 3 ms.

Figure 2:
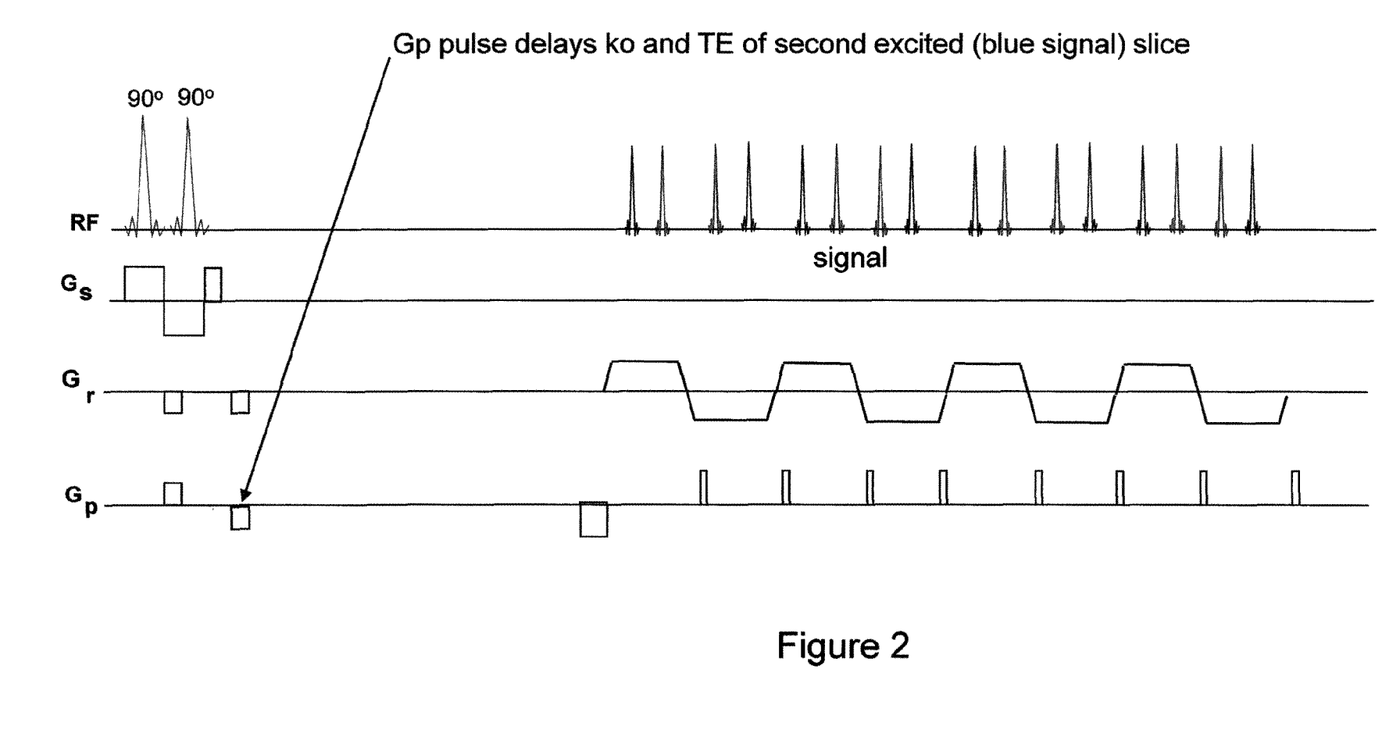
FIG. 2 illustrates another new method, which involves inserting additional Gp pulses between and after the excitation pulses.

Another method according to the new approach disclosed in this patent specification is illustrated in FIG. 2 and involves inserting additional Gp pulses between and after the excitation pulses, with or without the alternating Gs pulses, to force a delay upon the TE of the later-excited slices and cause all slices to have closer TE or even identical TE. The additional Gp gradient pulses seen in FIG. 2 shift the refocusing time of the center of k-space, ko, to a later signal within the echo train. In effect, different slices then have different sliding delays in their k-space data recorded in the echo train, and this normalizes the TE of slices to be the same or very close. FIG. 2 shows RF (radio frequency) pulses and Gs gradient pulses of the type used in FIG. 1b, but RF and Gs pulses as in FIG. 1a could be used in conjunction with the Gp pulses seen in FIG. 2.

FIG. 2 shows the addition of two pulses of opposite polarity on the phase encode axis Gp, creating a net zero phase effect in the first excited slice signals. The second excited slice does not experience the initial Gp pulse as its signal has not been created until after the second excitation pulse, and the second Gp pulse is experienced by slice 2 without the nulling effect on phase of the first Gp pulse. The second Gp pulse effectively creates a time delay or a time advancement of the entire phase encoding process including ko, of the later excited slice 2 with respect to slice 1 while both are still recorded in the same echo train.

A third technique disclosed in this patent specification of reducing TE, and reducing signal decay and dependent image distortions, is to reduce the echo spacing of different slices within the echo train. It has been discovered that both the multi-band (MB) technique and the SIR technique of exciting multiple slices can be performed with advantage by allowing the signals of two or more slices to directly overlap within each of the multiple analog-to-digital converter (ADC) read period of the echo train. The echoes (or signals) can be separated from one another by the following means. By phase cycling the RF excitation pulses during different TR periods of repeated image acquisitions, the different linear combination of simultaneously recorded signals from two or more TR periods can effectively be nearly perfectly separated. Two or more excitation pulses with differing phase can be combined in multi-banded RF pulses so that the signals are excited simultaneously to reduce delays up front, while their respective slice signals are simultaneously recorded within the echo train, rather than recording their respective echoes in an interleaved pattern within the echo train, the latter requiring overall longer time and larger time spacing between similar slice echoes. The larger number of slices can be separated using Hadamard encoding, however, additional TRs are required. The resulting images become the time average of the TR signals, hence a higher SNR by the square root of the number signals combined is resultant. The simultaneity of signal excitation and echo recording improves the image quality by proportionally reducing the amount of accumulative off-resonance phase error in the echo train and corresponding k-space of the resulting multiplexed EPI images. Principles of using MB-SIR techniques are disclosed in provisional application 61/394,929 filed Oct. 20, 2010, a copy of which is attached hereto as Appendix B to be made a part of the disclosure on this patent application. PCT application PCT/US2011/57161 filed Oct. 20, 2011 claims the benefit of said provisional application and is hereby incorporated by reference in this patent application.

Figure 3:
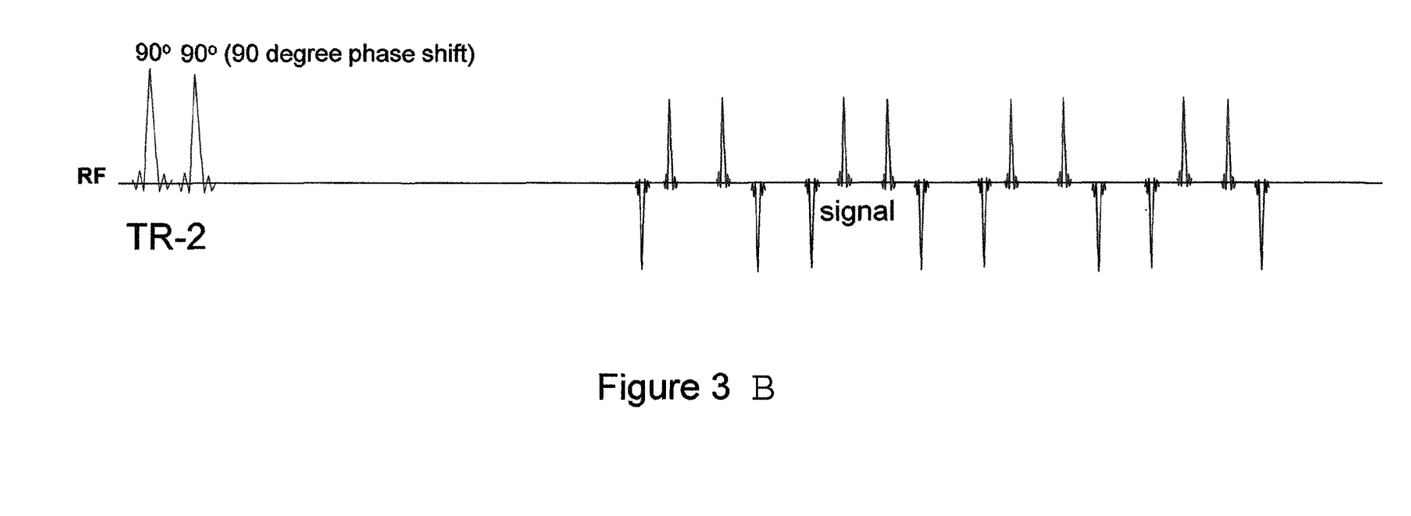
FIGS. 3a and 3b illustrate different phase cycled signals created to bring echoes closer together.
Figure 3A:
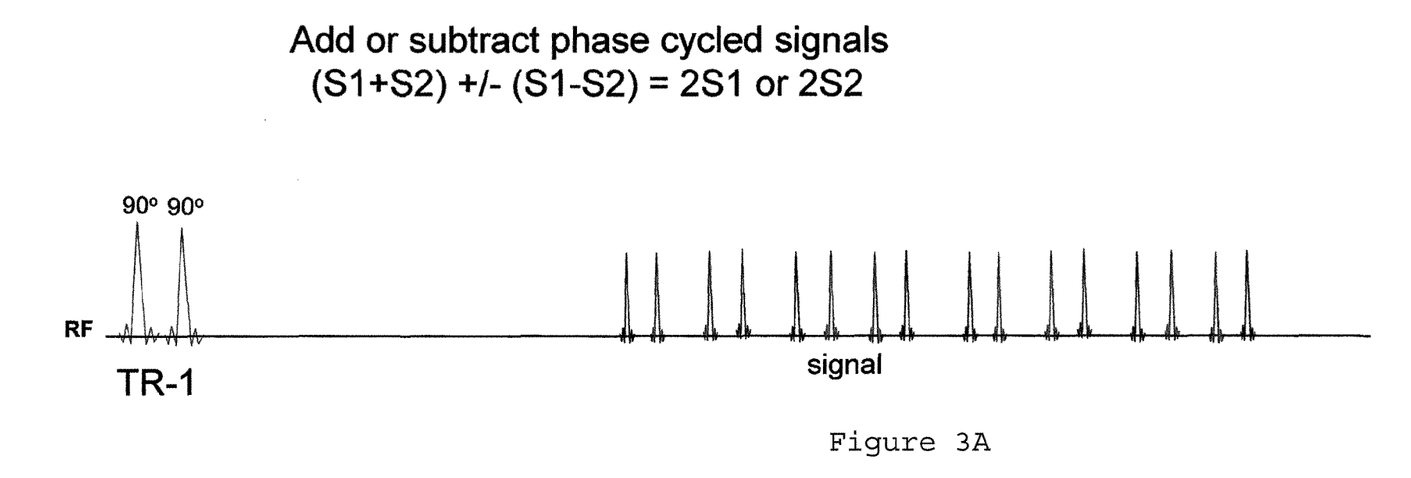

FIGS. 3a and 3b illustrate the different phase cycled signals created to bring the echoes closer together. In FIG. 3a, the slice signals for the two slices are all positive while in FIG. 3b the slice signals are positive for one of the slices but are negative for the other slice. Only the RF pulses and signals are shown in FIGS. 3a and 3b. The gradient waveforms of Gs, Gr and Gp can be the same as in FIG. 1a or 1b. While only two slices are illustrated in several of the examples, it should be understood that the principles disclosed here apply to pulse sequences that simultaneously excite more than two slices.

Figure 4A:
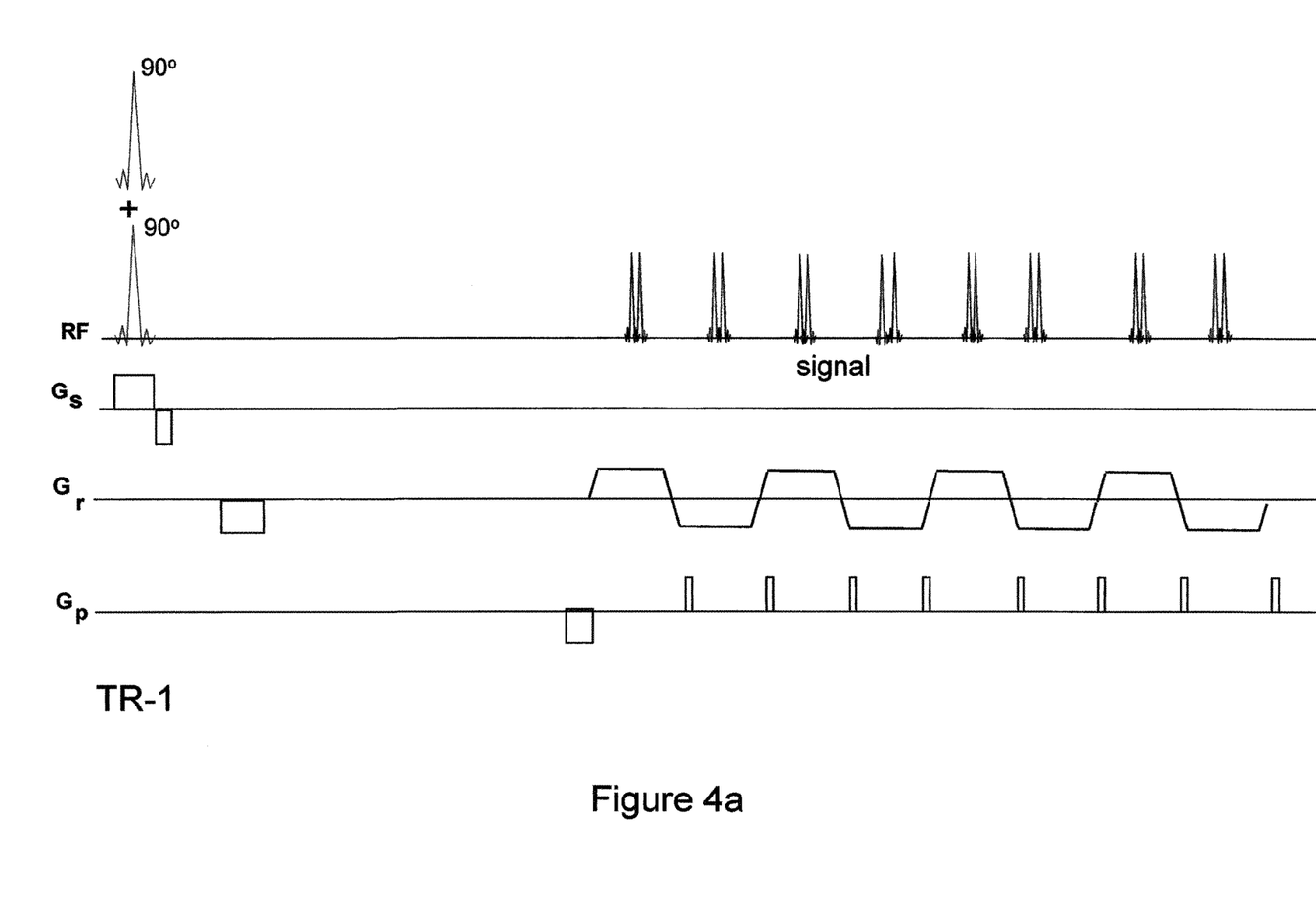
FIG. 4a illustrates another way in which a phase cycled RF pulse can be used in multi-banded pulses to record multiple EPI images with simultaneous signal recording within an echo train.
Figure 4B:
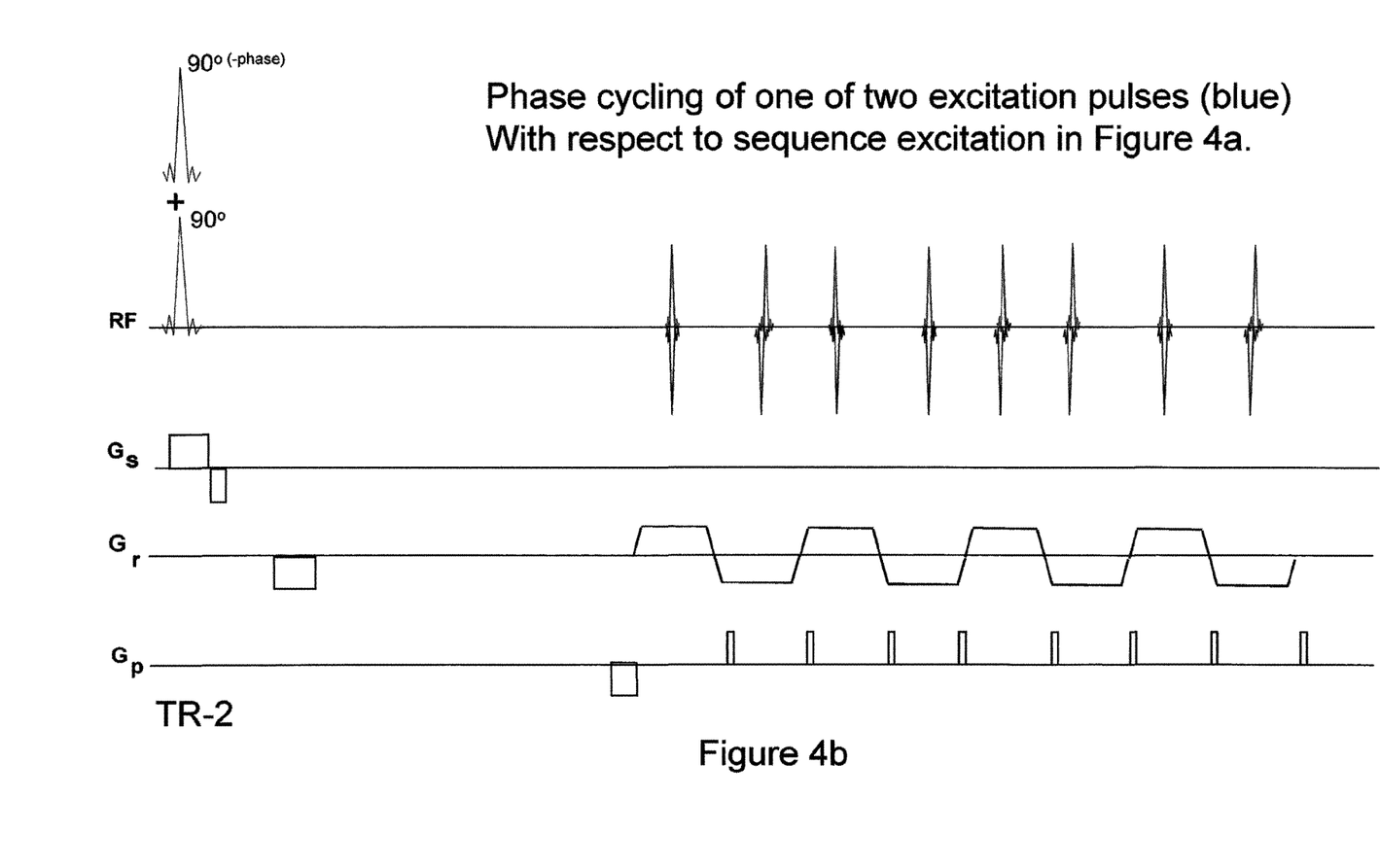
FIG. 4b is similar but illustrates the use of RF pulses of opposite phase, resulting in the MR signal being positive for one slice and negative for the next slice, with the two MR signals occurring essentially at the same time.

FIG. 4a illustrates another possible way in which a phase cycled RF pulse can be used in multi-banded pulses (simultaneous excitation by two or more phase and frequency offset RF excitation pulses), to record multiple EPI images with simultaneous signal recording within an echo train. FIG. 4b is similar but illustrates the use of RF pulses of opposite phase, resulting in the MR signal being positive for one of the slices and negative for the other slice, with the two MR signals occurring essentially at the same time.

Figure 5:
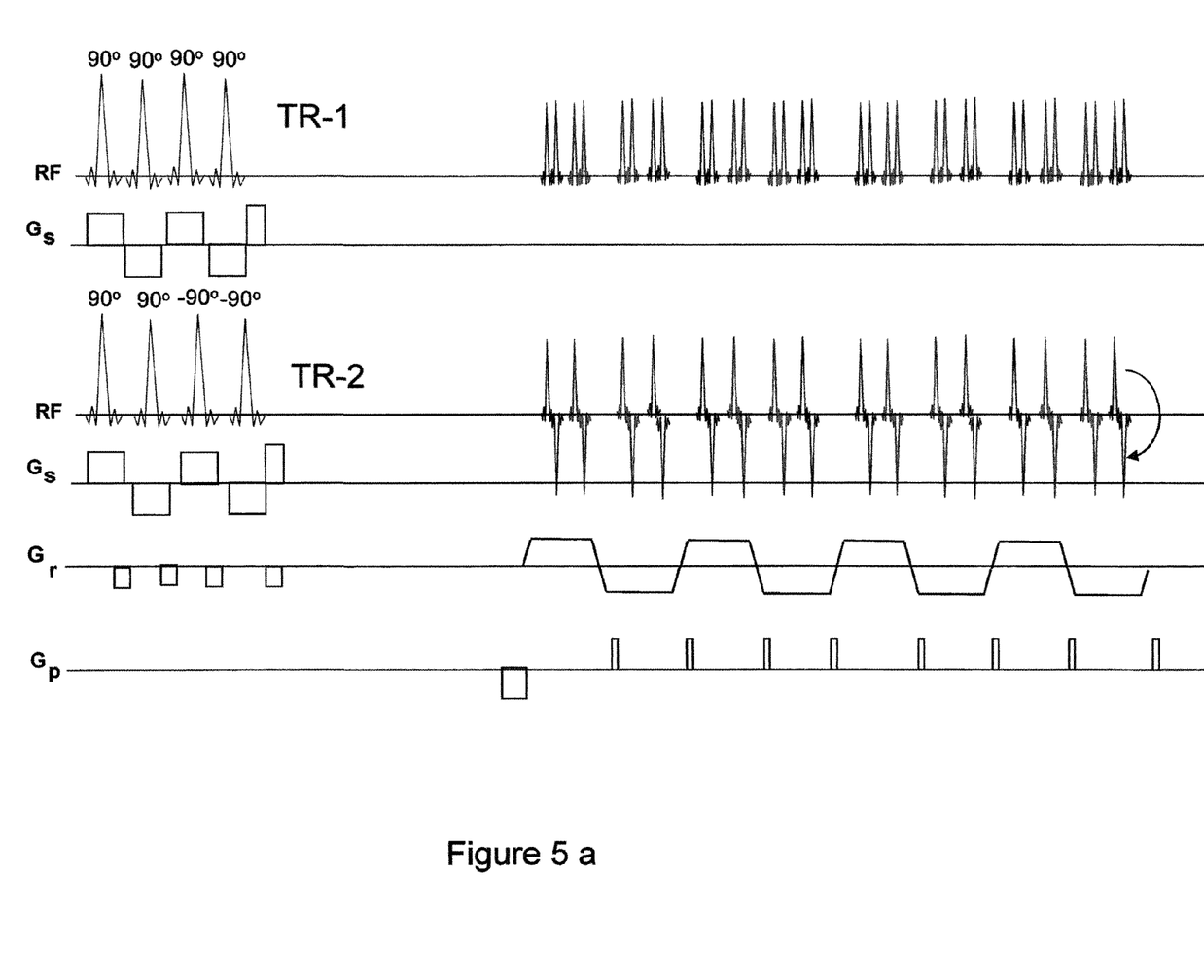
FIG. 5a illustrates a case TR-1 in which four RF excitation pulses are used to generate sets of four MR signals, and a case TR-2 in which two of the RF signals an (+90°) and the other two are (−90°).
FIG. 5b also illustrates two cases, showing how to achieve shorter echo train time using overlapped MR signals.

FIG. 5a illustrates a case TR-1 in which four RF excitation pulses are used to generate sets of four MR signals, and a case TR-2 in which two of the RF signals an (+90°) and the other two are (−90°). As a result, the MR signals for two of the slices are positive and those for the other two slices are negative, but the MR signals for each pair of slices occur essentially at the same time.

Figure 5B:
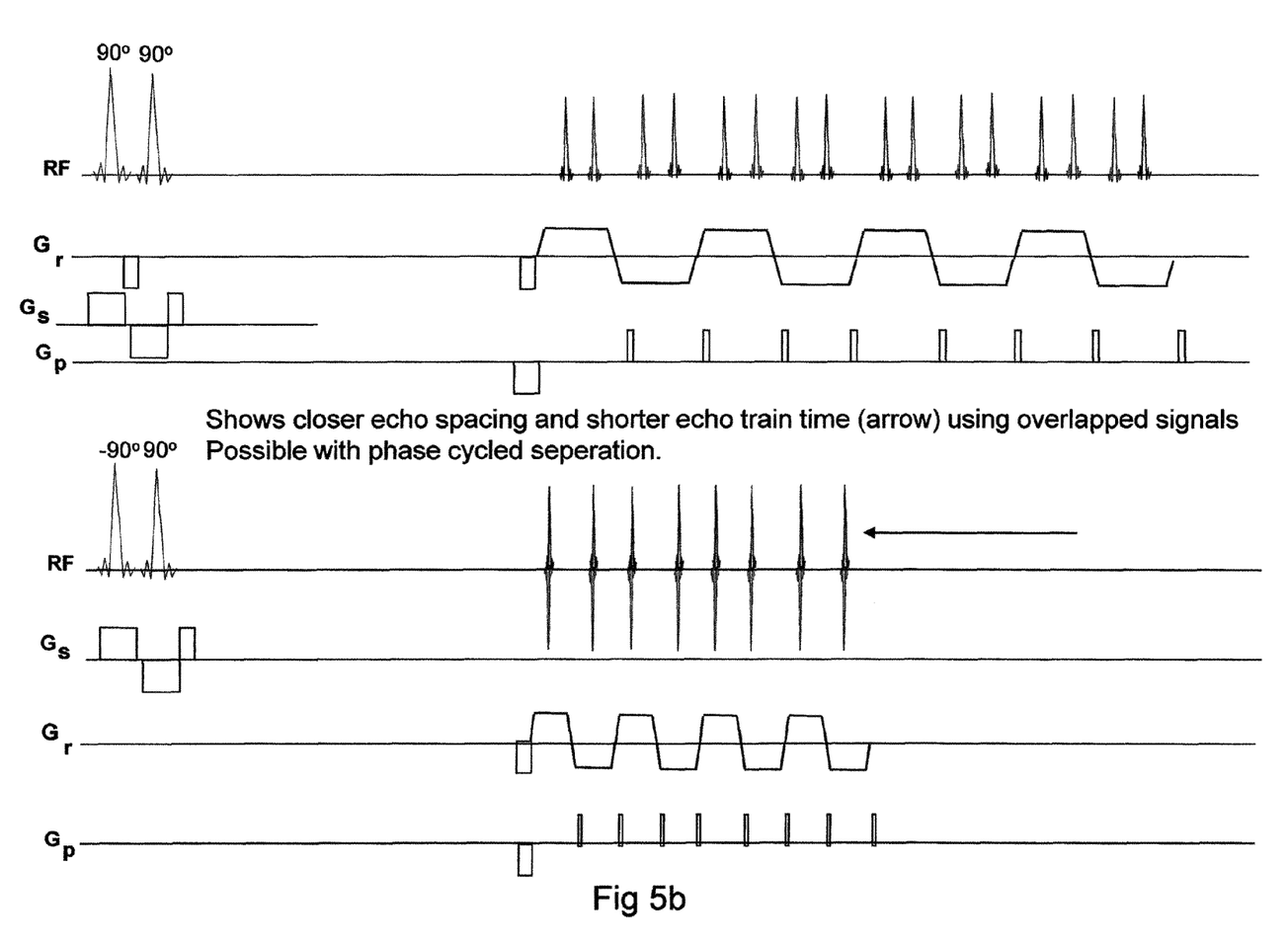

FIG. 5b also illustrates two cases, showing how to achieve shorter echo train time using overlapped MR signals. In the upper half of FIG. 5b, all MR signals are positive but in the lower half of FIG. 5b the RF pulses overlap (but have different signs) and the MR signals for the two slices also overlap, thus making the readout pulses shorter. The Gr pulses differ between the upper and lower portions of FIG. 5b.

Figure 6:
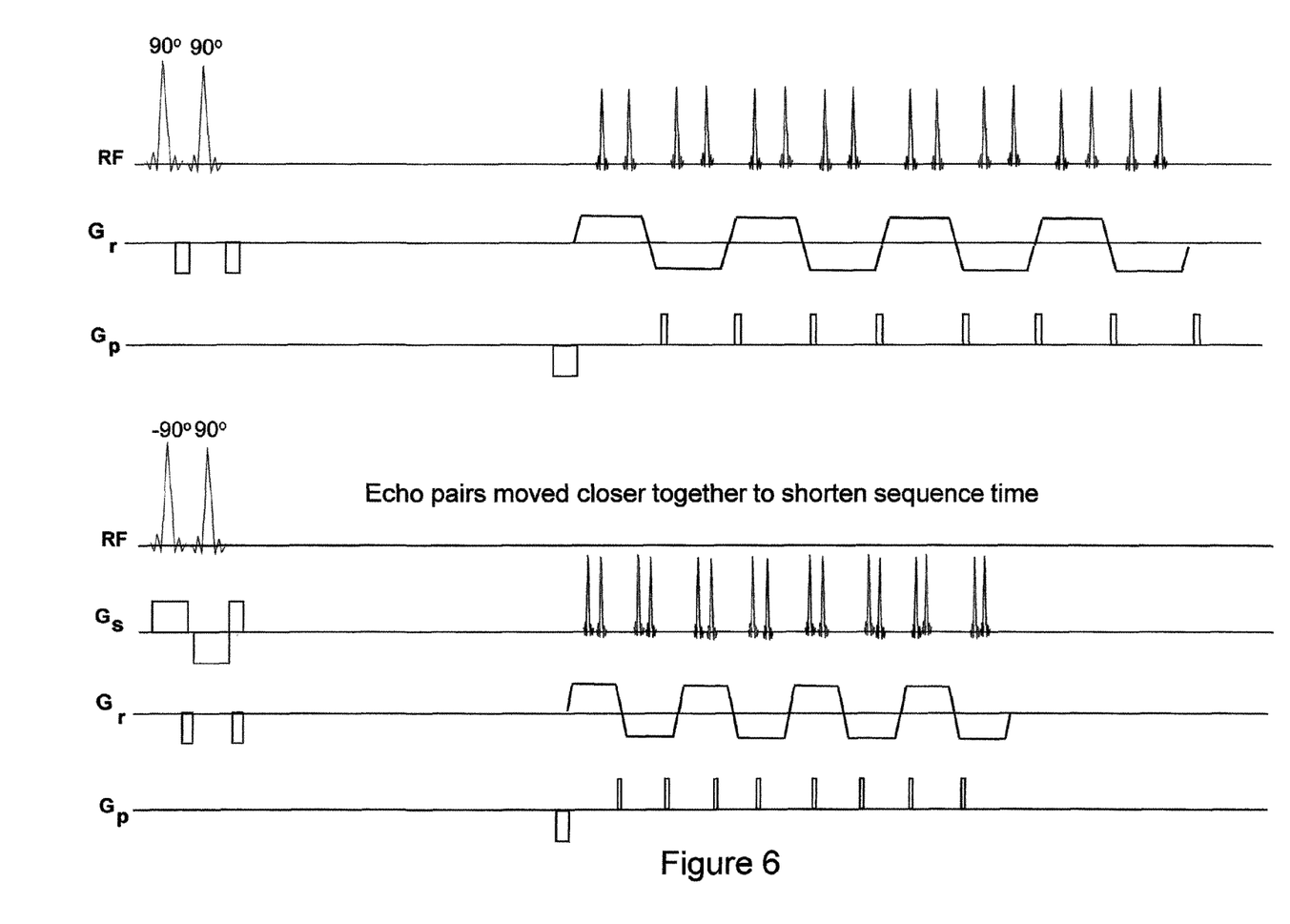
FIG. 6 illustrates, in the upper half, the use of FR pulses have the same sign and illustrates, in the lower half, the use of RF pulses that have opposite signs.

FIG. 6 illustrates another two cases. In the upper half of FIG. 6, the FR pulses have the same sign but have opposite signs in the case shown in the lower portion of FIG. 6. As a result, the echo pairs are closer together in the lower portion of FIG. 6

A way to reduce echo spacing and overall distortions is to use asymmetric positioning of the echoes from different slices, bringing them closer together on each ADC (analog-to-digital conversion) read period, or alternatively leaving them spaced the same but not recording the outer portion of each echo so as to shorten their respective kr coverage and at the same time reduce their required recording time. This results in a partial Fourier k-space coverage. However a small, ⅛ or more, zero filling of the k-space, which is complex conjugate symmetric, still leaves spatial frequencies on the non-zero padded quadrants of k-space, hence the resolution of the image is not substantially reduced whereas the distortions and off-resonance artifacts are reduced by means of the closer echo spacing.

Figure 7:
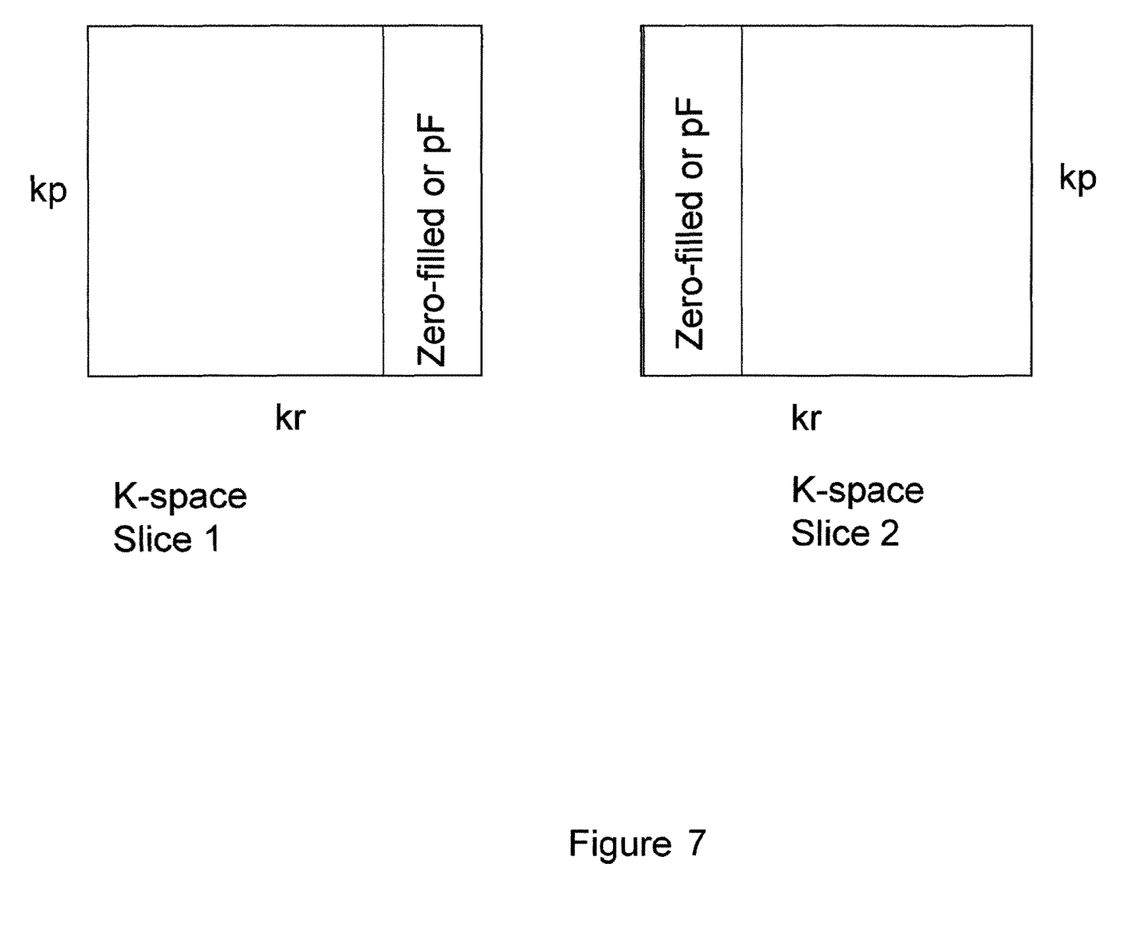
FIG. 7 illustrates k-space coverage where reduced k-space is covered with zero-filling of the matrix or partial Fourier reconstruction (pF) is used to reconstruct MR images.

FIG. 7 illustrates the corresponding k-space coverage. Reduced k-space is covered with zero-filling of the matrix or partial Fourier reconstruction (pF) is used to reconstruct MR images.

Instead of using zero filling of k-space, a model-based approach using information from multiple MRI coils using the MB technique can be applied to improve separation of overlapping MRI signals. Thus, information of the timing of the MR echo can be combined with coil sensitivity information. For example, MB/3×SIR3, the MB slices would be equally spaced on the z-axis while the 3 SIR echoes (which contain the MB slices) would also be equally spaced, positioned at ⅓ distance on the z-axis from each other and spaced on the Gr axis with overlap. Then both the coil sensitivity and timing would be different for each slice. A phase modulation for FOV/3 shift on the kp axis can be used, but the k-space separation of different MR signals would be greatly facilitated by two independent sources of information on kr (echo timing) and kp (aliased modulation) and independent information on z-axis coil intensity differences.

Further, the techniques described above can be combined with the method proposed for "z-blip Caiparinha" discussed in Setsompol K, et al., Improving SN per unit time in Diffusion Imaging using a plipped-CAIPARINHA simultaneous multi-slice acquisition, which is a paper incorporated by reference herein and attached as Appendix C to become a part of this patent application.

One important benefit of the new M-EPI approach, in which perfusion parameters for the entire brain or organ of interest can be obtained so rapidly, is that M-EPI scans of the organ can be taken repeatedly to thereby view dynamic changes and exchanges of blood between arterial, capillary and venous compartments. For example, 14 time-sequential blocks of 36 slice images each can be taken in an implementation of the teachings of this patent application so as to give useful guidance regarding the exchange of blood between different vascular compartments.

It should be apparent to those skilled in the art from the disclosure of this provisional application that the M-EPI sequence may be performed with setting either SIR=1 or MB=1, so that the acceleration is performed either with MB×SIR=1×SIR or SIR×1, hence with MB or SIR alone. Different MRI scanner hardware may have different RF coils and gradients so that it may be desirable to perform M-EPI in these more limited ways with useful but more restricted acceleration.

The following paper may provide additional background and is hereby incorporated by reference: Souza S P, et al., Simultaneous Multislice Acquisition of MR Images by Hadamard-Encoded Excitation, Journal of Computer Assisted Tomography, 12(6):1026-1030, November/December, © 1988 Raven Press, Ltd., New York. Further background may be found in provisional application No. 61/394,528 filed on May 28, 2010, which is attached hereto as Appendix D to become a part of this patent application. U.S. patent application Ser. No. 13/118,179 claims the benefit of said provisional application 61/394,528 and is hereby incorporated by reference in this patent application.

While specific examples have been described above, the new approach described in this patent specification is not limited to those examples and the scope of the invention encompasses other implementations as well.

The invention claimed is:

1. A magnetic resonance imaging (MRI) method comprising:
   applying, to a subject in an MRI scanner, a set of S radiofrequency (RF) multiband excitation pulses each of which simultaneously excites M respective slices in the subject in a simultaneous image refocusing pulse sequence, wherein S>1 and M>1;
   applying to the subject a set of slice selective magnetic gradient pulses on a Gs axis that alternate in polarity in a timed relationship with said RF excitation pulses, without requiring refocusing magnetic gradient pulses on the Gs axis timed with the RF pulses, thereby reducing time delays between onset of MRI signals created by the respective RF pulses;
   acquiring MRI signals with at least one set of RF receiver coils;
   computer-processing the MRI signals acquired with said RF receiver coils to produce magnetic resonance image data for respective slices of the subject; and
   further computer-processing at least some of said magnetic resonance image signals to produce magnetic resonance images of at least some of said slices of the subject.

2. The method of claim 1 in which each of said multiband excitation pulses comprises at least two RF pulses that have at least some overlap in time but are offset from each other in at least one of frequency and phase.

3. A magnetic resonance (MRI) scanner system comprising:
   an MRI scanner having a source of a steady magnetic field Bo, sources of gradient magnetic fields acting on an imaging volume of the MRI scanner for containing a subject, and an RF system selectively applying RF excitation pulses to the imaging space and receiving MRI signals from the imaging space and subject therein in response thereto;
   a control and signal processing computer system coupled with said RF system and said sources of gradient fields, said computer system being configured to cause said MRI scanner to:
   apply to said imaging space and subject therein, through said RF system, a set of S radiofrequency (RF) excitation pulses each of which is a multiband RF excitation pulse, thereby causing the imaging space and subject to emit a train of N sets of S MRI signals each, wherein S>1 and N>1;
   apply to said imaging space and subject therein slice selective magnetic gradient pulses on a Gs axis that alternate in polarity in a timed relationship with said RF excitation pulses, without requiring refocusing magnetic gradient pulses on the Gs axis timed with the RF pulses, thereby reducing time delays between onset of MRI signals created by the respective RF pulses;
   acquire the MRI signals through said RF system; and
   computer-process the MRI signals acquired through said RF system to produce magnetic resonance image data for said slices of the imaging space and subject.

4. The system of claim 3 in which said computer system is further configured to cause each of the RF multiband excitation pulses to comprise at least two RF pulses that overlap in time at least partially but are offset from each other in at least one of frequency and phase.

5. A magnetic resonance imaging (MRI) scanner comprising:
   a source of a steady magnetic field Bo, sources of gradient magnetic fields acting on a subject in an imaging volume of the MRI scanner, an RF system selectively applying RF excitation pulses to the subject and receiving MRI signals from the subject therein in response thereto, and a computer program product comprising computer-readable programs stored on a computer-readable medium in a non-transitory form which, when loaded on and executed by said MRI scanner, causes the MRI scanner to carry out the steps of:
   applying, to a subject in the MRI scanner, a set of S radiofrequency (RF) multiband excitation pulses each of which simultaneously excites M respective slices in the subject in a simultaneous image refocusing pulse sequence, wherein S>1 and M>1;
   applying to the subject a set of slice selective magnetic gradient pulses on a Gs axis that alternate in polarity in a timed relationship with said RF excitation pulses, without requiring refocusing magnetic gradient pulses on the Gs axis timed with the RF pulses, thereby reducing time delays between onset of MRI signals created by the respective RF pulses;
   acquiring MRI signals with at least one set of RF receiver coils;
   computer-processing the MRI signals acquired with said RF receiver coils to produce magnetic resonance image data for respective slices of the subject; and
   further computer-processing at least some of said magnetic resonance image signals to produce magnetic resonance images of at least some of said slices of the subject.

6. The computer program product of claim 5 wherein said programs cause the MRI scanner system to include in each of the RF multiband excitation pulses at least two RF pulses that are offset from each other in at least one of frequency and phase.

7. The computer program product of claim 6 in which the at least two RF pulses are offset in phase.

8. The computer program product of claim 6 in which the at least two RF pulses are opposite in phase.

9. The magnetic resonance imaging method of claim 1 in which the at least two RF pulses are offset in phase.

10. The magnetic resonance imaging method of claim 1 in which the at least two RF pulses are opposite in phase.

11. The magnetic resonance scanner system of claim 3 in which the at least two RF pulses are offset in phase.

12. The magnetic resonance scanner system of claim 3 in which the at least two RF pulses are opposite in phase.

* * * * *